US005598839A

United States Patent [19]
Niles et al.

[11] Patent Number: 5,598,839
[45] Date of Patent: Feb. 4, 1997

[54] POSITIVE EXPIRATORY PRESSURE DEVICE

[75] Inventors: Rex A. Niles, Oneida; Ronald McHenry, E. Syracuse; George Puderbaugh, Manlius; Stephen J. Scheuermann, Oneida, all of N.Y.

[73] Assignee: Diemolding Corporation, Canastota, N.Y.

[21] Appl. No.: 230,547

[22] Filed: Apr. 20, 1994

[51] Int. Cl.⁶ ........................................................ A62B 7/00
[52] U.S. Cl. ........................................ 128/205.23; 128/725
[58] Field of Search ........................... 128/205.23, 725, 128/728, 202.22, 205.24

[56] References Cited

U.S. PATENT DOCUMENTS

| | | | |
|---|---|---|---|
| 3,363,260 | 1/1968 | Garbe | 128/728 |
| 3,933,171 | 1/1976 | Hay | 137/493.7 |
| 3,993,050 | 11/1976 | Robinson et al. | 128/728 |
| 4,062,358 | 12/1977 | Kritzer . | |
| 4,158,360 | 6/1979 | Adams | 128/725 |
| 4,403,616 | 9/1983 | King | 128/725 |
| 4,421,120 | 12/1983 | Edwards, Jr. et al. | 128/725 |
| 4,446,863 | 5/1984 | Rubin et al. | 128/204.18 |
| 4,533,137 | 8/1985 | Sonne | 128/725 |
| 4,601,465 | 7/1986 | Roy | 128/207.16 |
| 4,706,685 | 11/1987 | Jones, Jr. et al. | 128/725 |
| 4,736,750 | 4/1988 | Valdespino et al. | 128/725 |
| 4,768,520 | 9/1988 | Varraux et al. | 128/725 |
| 4,944,306 | 7/1990 | Alvino | 128/725 |
| 5,320,107 | 6/1994 | O'Brien | 128/725 |

OTHER PUBLICATIONS

The Ambu PEP Mask System, p. 26.
Astra Meditec, The PEP/RMT–SET.
Mette Kelstrup & Merete Falk, Astra Meditec, Positive Expiratory Pressure (PEP) in Cystic Fibrosis.
Michael J. Mahlmeister et al., Positive–Expiratory–Pressure Mask Therapy: Theoretical and Practical, etc., Nov. 91, pp. 1218–1230.
Vitapep opens up new air ways for patients with secretory problems.
DC Lung Company, Inc., Resistex.

*Primary Examiner*—Aaron J. Lewis
*Attorney, Agent, or Firm*—August E. Roehrig, Jr.

[57] ABSTRACT

A single user respiratory therapy device including a pressure range monitoring unit which provides the patient with visual feed-back to monitor the correct use of the device for enhancing the benefits of positive expiratory pressure therapy.

10 Claims, 5 Drawing Sheets

POSITIVE EXPIRATORY PRESSURE DEVICE

BACKGROUND OF THE INVENTION

This invention relates in general to respiratory therapy devices and, in particular, to a respiratory therapy device for use by a single patient. More specifically, but without restriction to the particular use which is shown and described as the best mode contemplated for carrying out this invention, the invention relates to an inexpensive single user respiratory therapy device that provides substantially resistance free inhalation, and selectively controlled resistive exhalation, with a pressure range monitoring unit to provide the patient with visual feed-back to enable the patient to monitor the proper usage of the device.

Persons who suffer from pulmonary problems that result in large amounts of mucus being produced in the lungs often require assistance in the removal of these secretions. If these secretions are allowed to remain in the lungs, airway obstruction occurs resulting in poor oxygenation and possible pneumonia and/or death. One of the clinically recognized treatments for this condition is a technique known as positive expiratory pressure therapy or PEP. With PEP therapy, a patient exhales against a resistance to generate expiratory pressure at a substantially constant rate of flow. Prescribed expiratory pressures are generally in the range of 10–20 cm H2O, although other pressure ranges and pressures can be used.

PEP therapy has been documented by clinical research as equal to or superior to standard chest physiotherapy techniques which, while effective, are time consuming and not well tolerated by many patients who have difficulty breathing for extended periods of time in certain positions required for administration of standard chest physiotherapy. Accordingly, PEP therapy is believed to provide significant advantages to patients suffering from cystic fibrosis, and is felt to be an eventual replacement for chest physiotherapy for many patients.

In the use of PEP therapy, a patient breathes through an orifice restricter to generate a positive pressure in the lungs during exhalation, with the pressure falling to zero at the end of exhalation. By selection of a proper-sized orifice, a given pressure is determined for the exhalation flow rate generated by an individual patient. This extended, substantially constant flow, elevated-pressure exhalation has been shown to be effective for moving secretions trapped in the lungs to the larger airways where they can then be removed through coughing.

The PEP therapy devices presently in use are very effective in the administration of the PEP therapy. However, these devices require the use of an expensive pressure gauge, which is not a part of the PEP device, but separately connected to the device when in use. With such devices, unless the hospital or patient purchases an expensive pressure gauge to connect to the device, the patient is unable to monitor its use. Without the ability to monitor the expiratory pressure, the patient is unable to determine if the PEP therapy technique is being properly administered.

While an expensive pressure gauge can be connected to the device to display the expiratory pressure being exerted by the patient, proper administration of the PEP therapy does not require the determination by the patient of an exact gauge pressure. The PEP therapy can be properly administered as long as the patient can be made aware when the device is in use that the expiratory pressure is being maintained within a proper predetermined pressure range.

SUMMARY OF THE INVENTION

It is, therefore, an object of this invention to improve single user respiratory therapy devices.

Another object of this invention is to incorporate a pressure range monitoring unit having visual feed-back for a patient as an integral portion of a single user respiratory therapy device.

A further object of this invention is to incorporate a low-cost pressure monitor as an integral component of a single user respiratory therapy device.

These and other objects of this invention are attained in accordance with the present invention wherein there is provided a single user respiratory therapy device including a pressure range monitoring unit which provides the patient with visual feed-back to monitor the correct use of the device for enhancing the benefits of positive expiratory pressure therapy.

DESCRIPTION OF THE DRAWINGS

Further objects of the invention together with additional features contributing thereto and advantages accruing therefrom will be apparent from the following description of a preferred embodiment of the invention which is shown in the accompanying drawings with like reference numerals indicating corresponding parts throughout, wherein.

DESCRIPTION OF THE PREFERRED EMBODIMENTS

Figure 1:
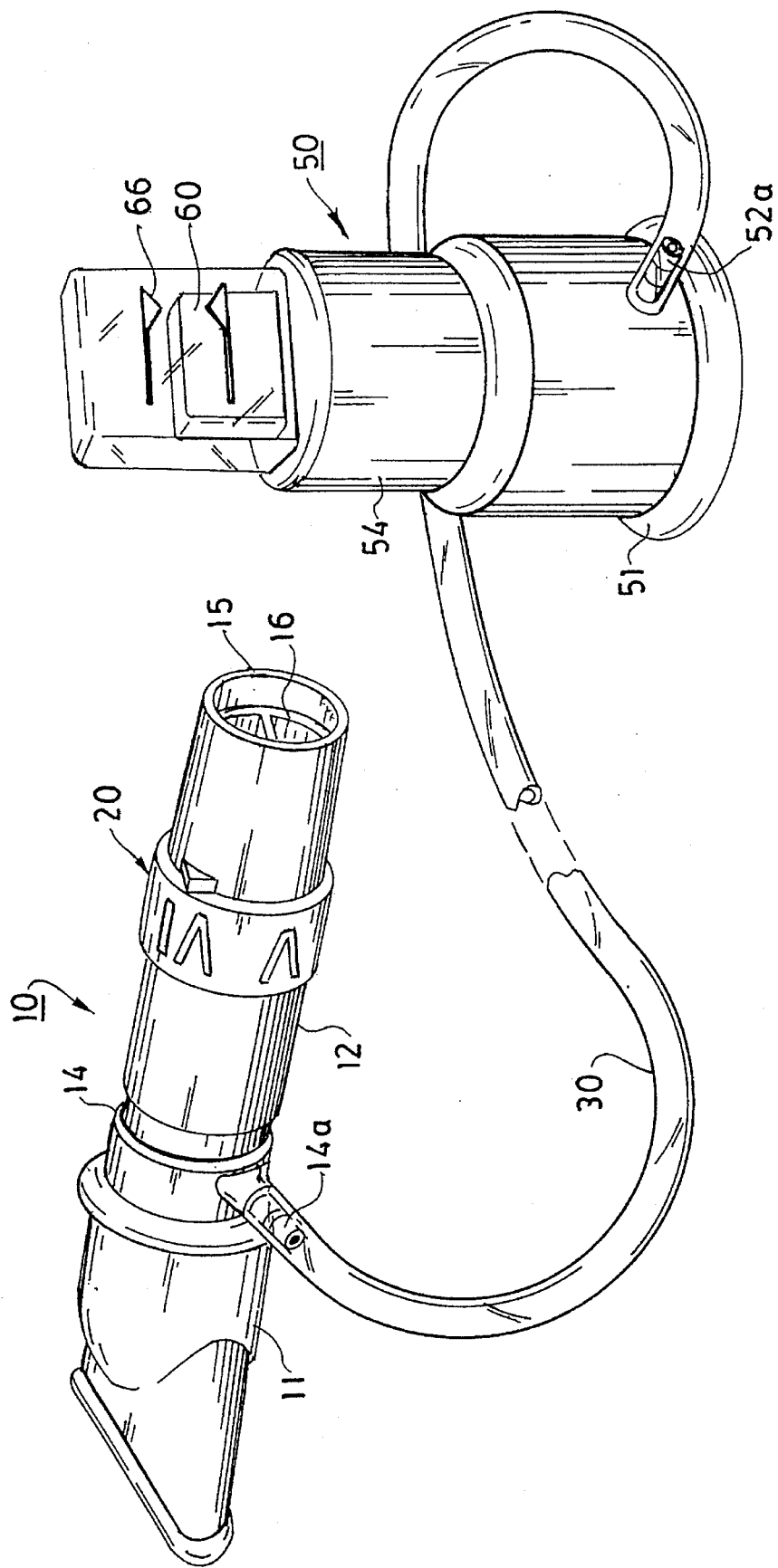
FIG. 1 is a perspective view of a single patient use respiratory therapy device incorporating a pressure range monitoring unit to provide the user with visual feed-back for monitoring the administration of positive expiratory pressure (PEP) therapy.

Referring now to the drawings, there is shown in FIG. 1 a PEP therapy device constructed in accordance with the present invention. The device includes a patient input portion 10, through which a patient breathes, connected to a pressure range monitor portion 50 by a flexible conduit 30 through which expiratory air pressure is coupled for a purpose and in a manner to be described in detail hereinafter. The input portion 10 includes an expiratory pressure controller 20, or orifice selector for setting the appropriate expiratory flow/pressure relationship for the patient's condition for therapy purposes. The pressure range monitor portion 50 provides a visual indicator to the patient that the expiratory pressure being applied is in the predetermined desired range for proper therapy administration. The pressure range monitor 50 has a removable base 51 for cleaning purposes to permit the cleaning of condensate which might accumulate.

Figure 2:
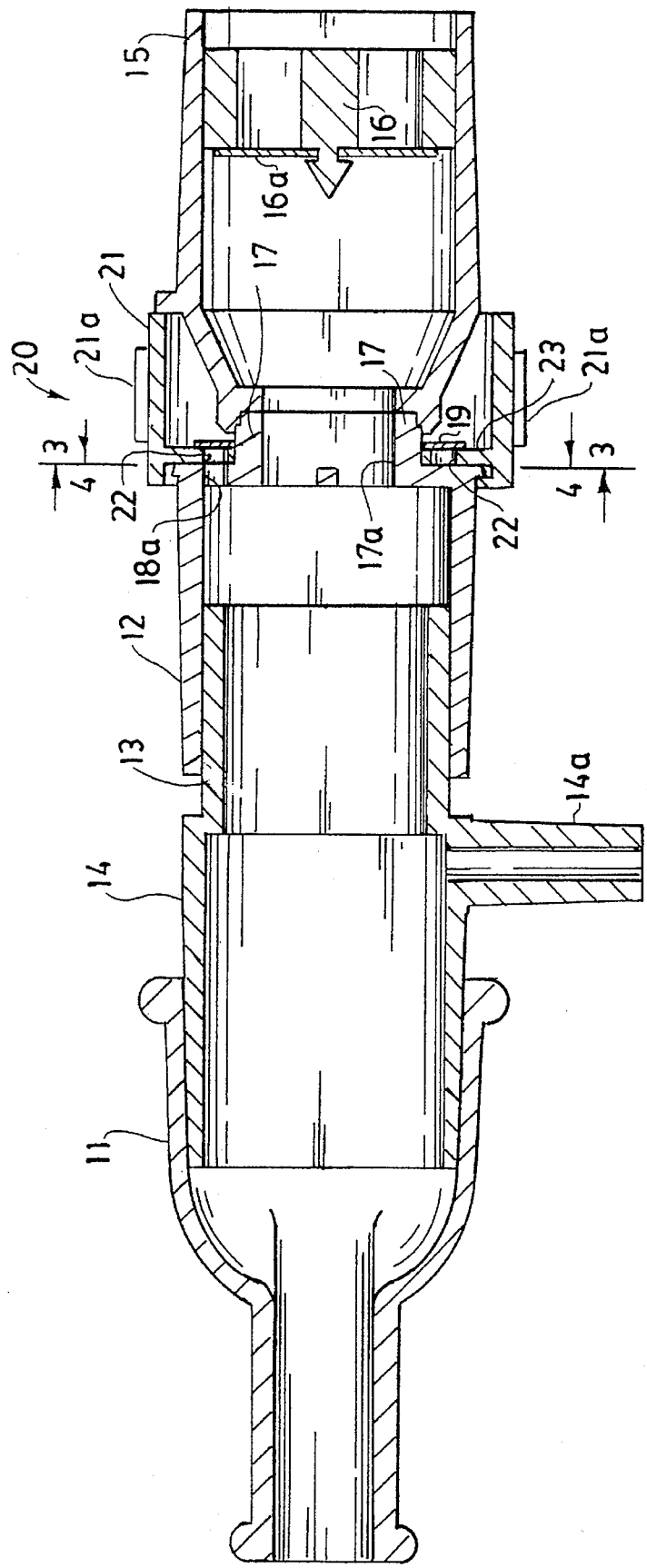
FIG. 2 is an enlarged cross-sectional view of a portion of the PEP device shown in FIG. 1 to better illustrate the patient input portion of the device.

The input portion 10 includes a mouthpiece 11 through which the patient breathes into the device. As shown in FIGS. 1, 2, 5 and 6, the mouthpiece 11 is of the type wherein the patient takes the part into the mouth, but the device is not intended to be limited to such applications. A standard mask 61, such as shown in FIG. 7 as a commercially available anesthesia mask, or a trach adapter can also be utilized. To this end the input body 12 is sized to have a mask/mouthpiece receiving port 13 of 22 mm OD to accept a standard 22 mm ID mouthpiece or a 22 mm ID mask, as well as an inlet port 15 of 22 mm OD to accept a standard 22 mm ID fitting for connection to standard respiratory equipment. As best shown in FIGS. 1 and 2, a preferred embodiment incorporated a tee portion 14 between the mouthpiece 11 and input body 12. The tee portion 14 has a discharge port 14a for connecting to conduit 30.

The inlet port 15 incorporates a one-way valve 16 to allow a patient to breath in, but prevents breathing out through the inlet 15. This one-way valve in the preferred embodiment is preferably made of a rigid injection-molded plastic frame and a flexible silicone rubber disc 16a. In use, air is drawn into the input body 12 through the one-way valve 16, positioned at the inlet port 15, which opens to allow the patient to inhale substantially resistance free. Upon exhalation, air is prevented from exiting through the inlet port 15 by the closing of this valve. Therefore, the expiratory air must exit through an expiratory pressure controller 20 incorporated in the input body 12 in a manner to be hereinafter described in detail.

Figure 10:
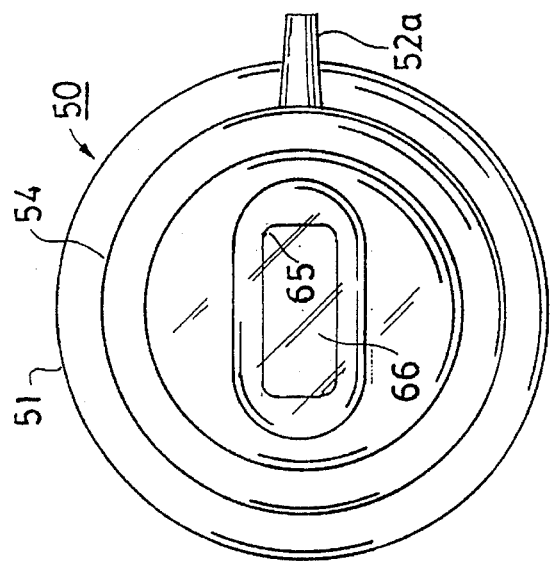
FIG. 10 is an enlarged horizontal elevation view of the pressure range monitoring portion of the device shown in FIG. 1 to better illustrate the positional relationship of the components thereof.
Figure 9:
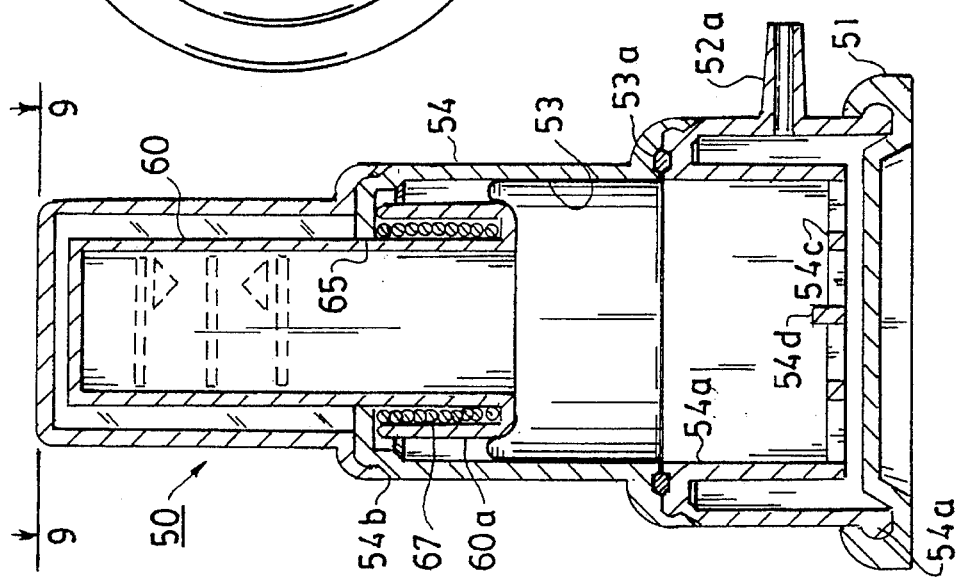
FIG. 9 is an enlarged cross-sectional view of the pressure range monitoring portion of the device shown in FIG. 1 to better illustrate the components thereof upon the application of pressure thereto.
Figure 8:
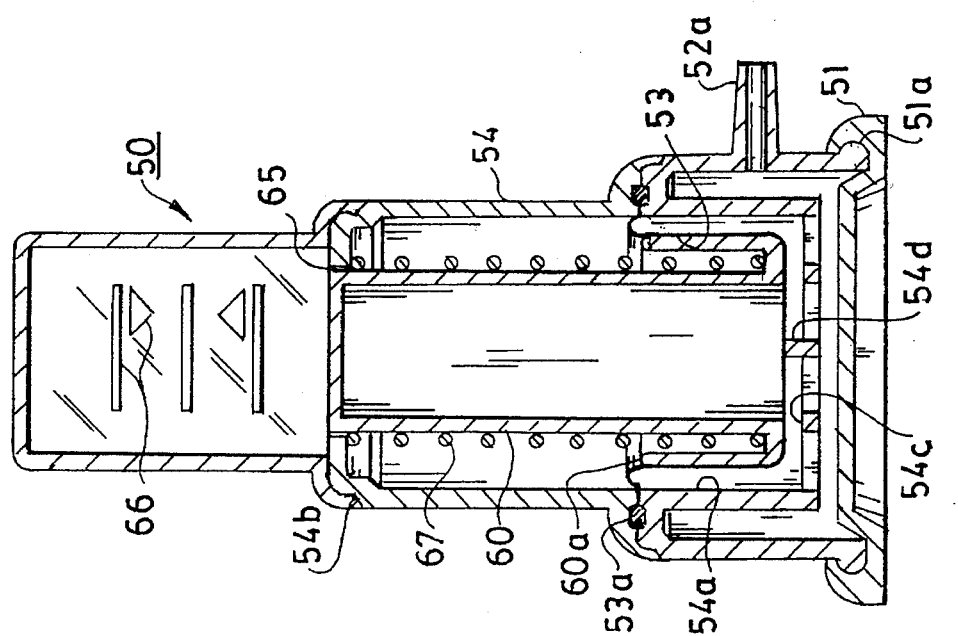
FIG. 8 is an enlarged cross-sectional view of the pressure range monitoring portion of the device shown in FIG. 1 to better illustrate the components thereof prior to the application of pressure thereto.

In order for a patient to be able to monitor the device when in use, to ensure that the PEP therapy is being properly administered, the input body 12 is connected to the pressure range monitoring unit 50, the details of which are best illustrated in FIGS. 8–10. A flexible conduit 30 is coupled at one end to the tee body 14, through the pressure port 14a, to apply the air pressure created by the patient during exhalation to the pressure range monitoring unit 50, through the pressure inlet port 52a.

The pressure range monitoring unit 50 includes a bellows 53 carried within a housing 54. The interior of the housing 54 is formed with a sealed lower portion 54a defined by the inner face of bellows seal 53 with the only air inlet or outlet being the pressure inlet port 52a through which pressurized air is introduced when a patient exhales into the mouthpiece 11. Effecting the seal for the housing 54 is the bellows seal 53 which is sealed by an "O" ring 53a, which is an integral part of the bellows seal 53, between an upper and the sealed lower portions of the housing 54 to effect a seal therebetween. The upper portion or top of the housing 54b is joined to the lower portion 54a of the housing 54 to capture the O-ring 53a therebetween effecting a pressure tight seal between bellows seal 53 and the lower portion 54a of the housing. The upper portion 54b of the housing 54 is open to atmosphere allowing air to escape from the upper portion thereby permitting the pressure differential to move the indicator 60. In this manner when air pressure is introduced into the housing through the pressure inlet port 52a, the bellows 53 will be moved in response to the increase in air pressure.

As previously disclosed, in the preferred embodiment the housing 54 locks air-tight into the base 51 when in use. Because the base 51 can be removed, for example to rinse the pressure chamber with disinfectant, a protective grate 54c is formed as a portion of the open end of the housing 54 to protect the bellows 53 when the base 51 is so removed. A stop 54d, best illustrated in FIGS. 8 and 9, is carried by the grate 54c to limit the downward travel of the indicator 60. When assembled, the base 51 forms a snap-lock seal with complementary ridges 51a on the open end of the housing 54 so an effective air-tight seal is formed. Other manners of making a suitable removable air-tight seal, such as a twist-lock or threaded cap, would be known to those skilled in the art. In addition, the base 51 could be permanently sealed if the removal feature was not desired.

To enable the patient to monitor the exhalation pressure being exerted when exhaling, an indicator 60 is utilized which provides a visual display to the patient when the invention is in use. For this purpose the indicator 60 is secured at a lower end to the top of the bellows seal 53, to the closed face thereof, and extends upwardly within the top portion 54b of the housing 54. The indicator 60 extends upwardly through an opening in a flange portion 65 such that the end thereof is guided during movement by the flange 65, the lower face of which functions as a stop for one end of a compression spring 67. The compression spring 67 is supported about the indicator 60 with its other end carried within an upturned cup portion 60a of the indicator 60. The uppermost end or rim of upturned or cup portion 60a also functions as a stop to limit the upward travel of the indicator 60 by engaging the flange 65. A further beneficial result obtained from using the cupped shaped upturned portion 60a is that during movement the bellows seal 53 is properly formed to keep it round. This prevents the bellows seal 53 from developing corners which could increase seal drag or resistance to movement.

The compression spring 67 provides a force against movement of the bellows 53 so that the amount of pressure applied within the housing 54 by the patients exhalation provides a nearly linear relationship with movement of the indicator 60. Accordingly, the spring 67 is designed to give a linear or nearly linear movement to the indicator 60 with increasing pressure in the housing 54. To facilitate expiratory pressure being applied against the closed face of the bellows 53 when a patient begins use of the invention, the at rest position of the bellows 53 against the stop 54d spaces the face thereof off the housing floor as best shown in FIG. 8.

This upper portion 54b of the housing 54 also has indicator markings 66 carried thereon to display to the patient when a predetermined expiratory pressure is being applied. In the embodiment illustrated, when the indicator top is lined up with the lower marking or line, the pressure is at the bottom of the prescribed range. When the indicator top lines up with the upper mark, the pressure is at the top of the pressure range. When the indicator top is in between the upper and lower markings, the pressure is in the correct range for administration of the proper therapy. While this is the preferable manner of providing the patient with a visual display that the invention is being properly used, alternatively the indicator 60 may be marked with indicia, such as a band, or bands, of color which when visible corresponds to the presence of a desired pressure being exerted by the patient.

Figure 3:
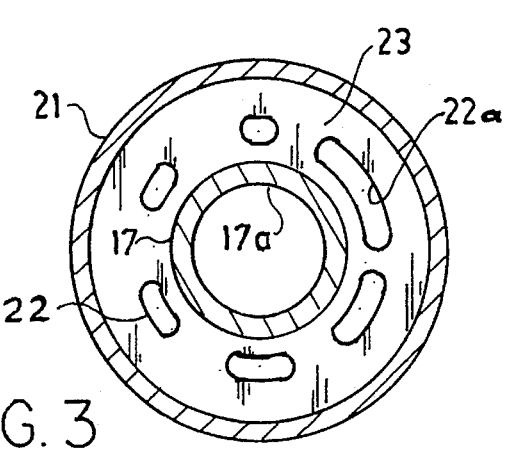
FIGS. 3 and 4 are cross-sectional views of the patient input portion of the device illustrated in FIG. 1 taken in the direction of lines 3—3 and 4—4 of FIG. 2 to better illustrate the internal structure thereof.
Figure 4:
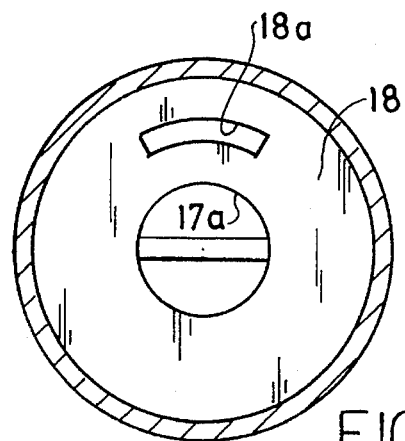

As previously disclosed, in order for a patient to create a desired expiratory pressure, the expiratory pressure controller 20 is incorporated into the input body 12. The expiratory pressure controller 20, the internal construction of which is best illustrated in FIGS. 2–4, is positioned in the input body to control the flow rate of the patient's expiratory air, and thereby induce a desired expiratory pressure in the patient's lungs which can be monitored by the pressure range monitoring unit 50. The controller 20 includes a selector dial 21 having indicia 21a marked thereon to correspond to different-sized openings 22 formed in an apertured face plate 23 which functions to support the selector dial 21 for selective rotation upon a hub 17 formed within the input body 12. While a preferred embodiment utilizes different-sized openings 22 in the face plate 23, it is to be understood that an alternative embodiment could utilize a slot, shown by reference numeral 22a, in the face plate 23 so that the slot 22a can be positioned relative to the opening 18a in plate 18 to vary the size of the opening through which air is passed. The hub 17 is supported within the input body 12 by a plate 18 which closes the interior of the input body 12 to the passage of air except through an aperture 18a formed therein and the open interior portion of the hub 17.

In operation, when a patient inhales air is drawn into the input body 12 through the inlet 15, through the one-way valve 16, and passes through the central opening 17a of hub 17 whereby the air is freely drawn into the patient's lungs substantially resistance free. When the patient exhales, however, the one-way valve 16 closes preventing discharge of air out through the opening 17a in the hub and the inlet 15 of the input body. Upon exhalation air is permitted to discharge only through the opening 18a and one of the selected openings 22 of the selector dial 21 when aligned therewith. A one-way outlet valve 19, through which the expiratory air is passed, assures that upon inspiration all air comes through the inlet. In this manner, there will be no dilution of any adjunct therapies which might be connected to the inlet 15 of the input body 12 for use in conjunction with the device, such as aerosolized medicine or an incentive spirometer.

The flow of expiratory air controlled in this manner passes out through a one-way valve 19, and is discharged from the input body 12 through the space between the input body and the selector dial 21. Because the flow rate of expiratory air is so controlled, a back pressure is created in the patient's lungs, which is also applied to the pressure range monitor 50 through the pressure port 14a to enable the patient to monitor the expiratory air pressure. By selectively rotating the dial 21, different sized openings can be utilized to control the expiratory air discharge rate and, therefore, the expiratory air pressure applied by the patient.

Figure 5:
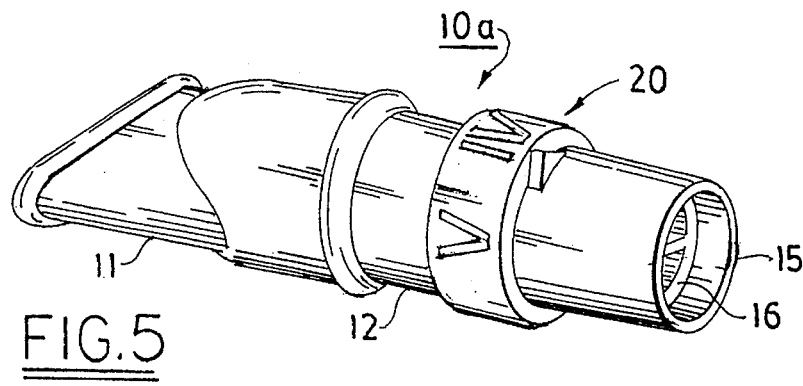
FIG. 5 is a perspective view of a modification to the patient input portion of the device.
Figure 6:
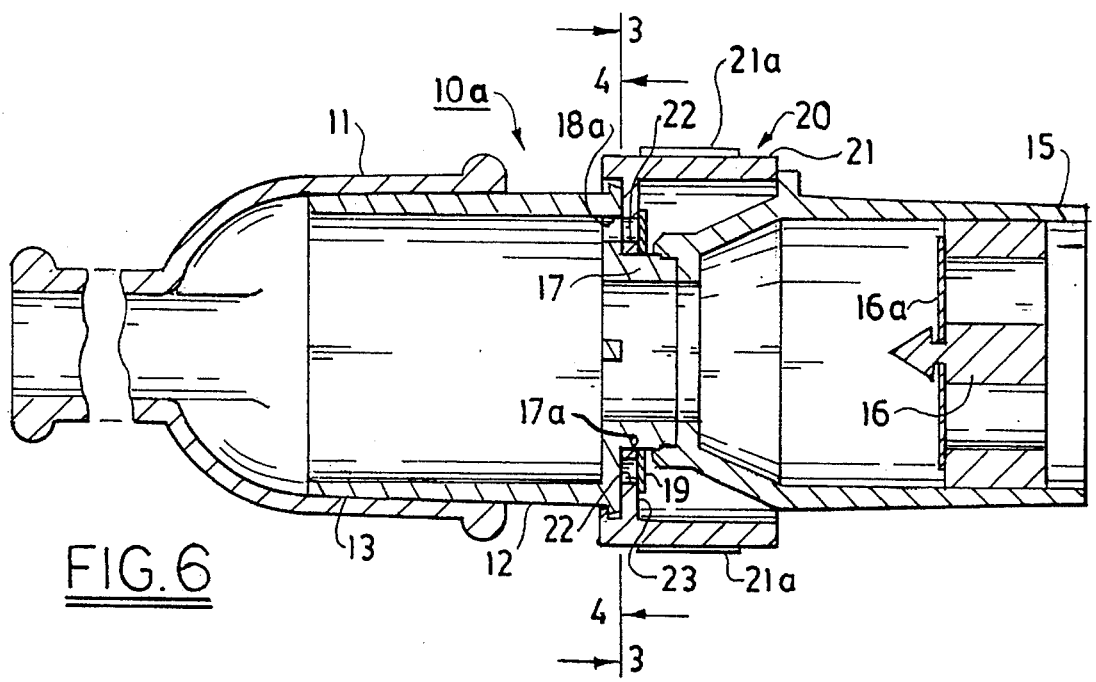
FIG. 6 is an enlarged cross-sectional view of the device illustrated in FIG. 5.
Figure 7:
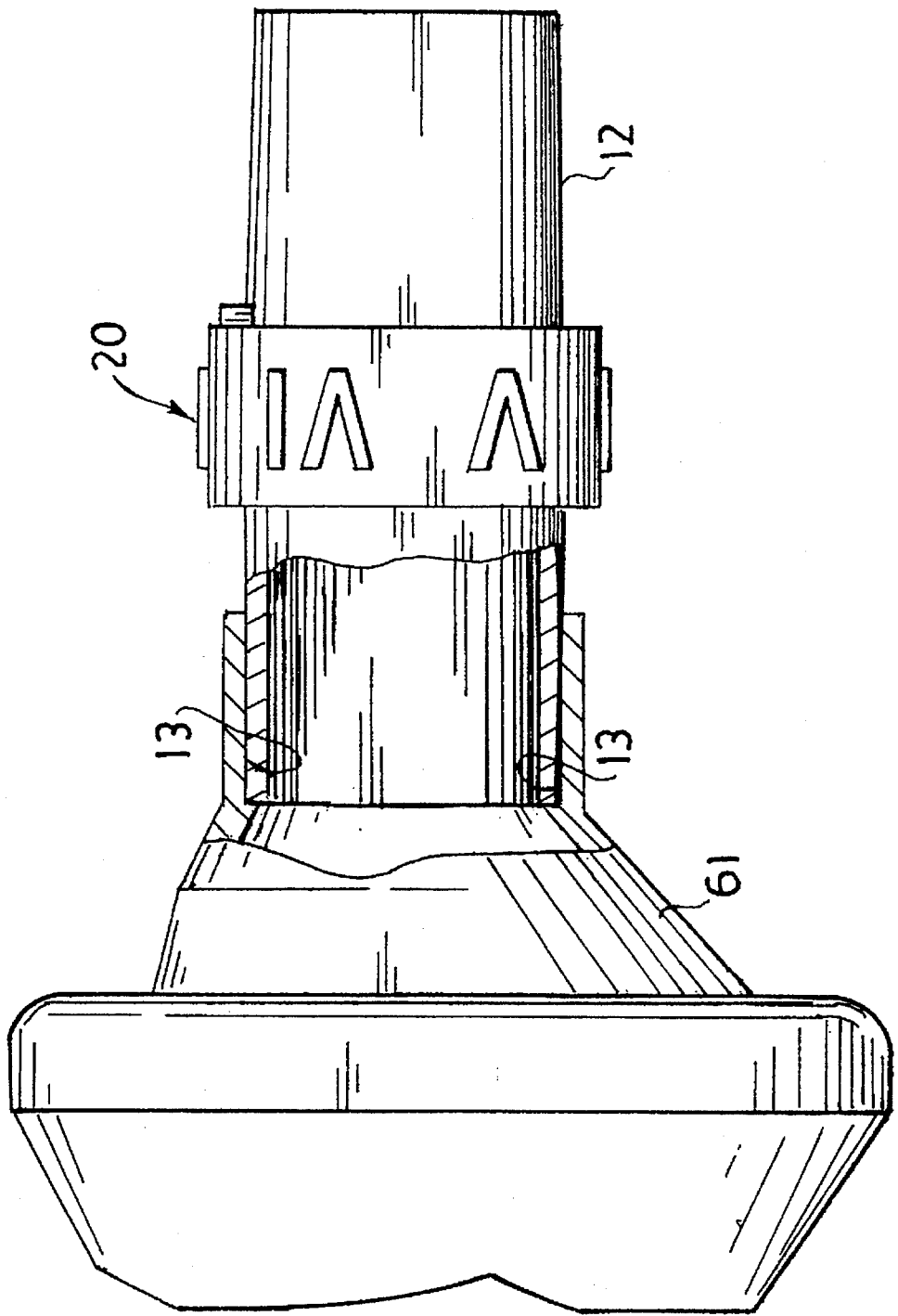
FIG. 7 is an enlarged view of a further modification to the patient input portion of the device with a portion broken away to illustrate the manner in which the device may be modified to accommodate another manner of patient input.

In the embodiment shown in FIGS. 5 and 6, where like reference numerals indicate parts corresponding to those previously described, the mouthpiece can be connected directly to the input body 12 without the tee portion 14. This would allow a patient to perform short term therapy, relying on the patients ability to feel the lung pressure generated to approximate, by memory, the correct pressure range. However, the patient would not be able to have a visual monitor of the pressure being applied, and such use is not recommended other than for short time periods.

While the invention has been described with reference to preferred embodiments, it will be understood by those skilled in the art that various changes may be made and equivalents may be substituted for elements thereof without departing from the invention. In addition, many modifications may be made to adapt a particular situation or material to the teachings of the invention without departing from the essential scope thereof. Therefore, it is intended that the invention not be limited to the particular embodiments disclosed in the specification and shown in the drawings as the best way presently known for carrying out this invention, but that the invention will include all embodiments falling within the scope of the appended claims.

What is claimed is:

1. A respiratory therapy device which monitors selectively controlled resistance exhalation comprising a housing having an outlet opening through which a patient to be treated passes expiratory air, and an input opening into which a patient to be treated exhales for establishing a patient-generated expiratory air flow, air flow control means carried by said housing for controlling the flow rate of expiratory air passing from said outlet opening to thereby induce an expiratory pressure in the patient's lungs upon generation of the expiratory air flow, said air flow control means movably operable to selectively vary the flow rate of expiratory air passing from said outlet opening for changing the expiratory pressure in response thereto and including a fixed plate having an orifice formed therein through which expiratory air is passed to said outlet opening, and a rotatable plate coaxially aligned therewith and having a plurality of different sized openings formed therein, each one of said different sized opening in said rotatable plate being mutually exclusively positionable into alignment with said orifice formed in said fixed plate to control the flow rate of expiratory air passed therethrough, a pressure monitor operatively connected to said housing between said input opening and said outlet opening, said pressure monitor actuable in response to the expiratory pressure in said housing, and indicia means integrally connected with said pressure monitor to enable a patient to establish and maintain a desired expiratory air pressure in response to said indicia means.

2. The respiratory therapy device as in claim 1 further including one-way valve means carried by said housing to pass inspiratory air thereinto substantially resistance free, and to prevent discharge of expiratory air from said housing except through said outlet opening.

3. The respiratory therapy device as in claim 2 further including a mouthpiece coupled to said input opening of said housing for facilitating the discharge of patient-generated expiratory air thereinto.

4. The respiratory therapy device as in claim 2 further including a mask coupled to said input opening of said housing for engaging at least a portion of a patient's face to facilitate the discharge of patient-generated expiratory air thereinto.

5. The respiratory therapy device as in claim 2 wherein said pressure monitor includes a sealed chamber having a seal movable in response to changes in the expiratory pressure applied to said pressure monitor.

6. The respiratory therapy device as in claim 5 further including means for biasing the movement of said seal against the expiratory pressure applied to said pressure monitor.

7. The respiratory therapy device as in claim 6 wherein said indicia means is supported by said seal for movement therewith.

8. A respiratory therapy device which monitors selectively controlled resistance exhalation comprising a housing having an outlet opening through which a patient to be treated passes expiratory air, and an input opening into which a patient to be treated exhales for establishing a patient-generated expiratory air flow, air flow control means carried by said housing for controlling the flow rate of expiratory air passing from said outlet opening to thereby induce an expiratory pressure in the patient's lungs upon generation of the expiratory air flow, said air flow control means movably operable to selectively vary the flow rate of expiratory air passing from said outlet opening for changing the expiratory pressure in response thereto and including a fixed plate having an orifice formed therein through which expiratory air is passed to said outlet opening, and a rotatable plate coaxially aligned therewith and having a slot formed therein, said slot being positionable relative said orifice formed in said fixed plate to control the flow rate of expiratory air passed therethrough, a pressure monitor operatively connected to said housing between said input opening and said outlet opening, said pressure monitor actuable in response to the expiratory pressure in said housing, and indicia means integrally connected with said pressure monitor to enable a patient to establish and maintain a desired expiratory air pressure in response to said indicia means.

9. A respiratory therapy device comprising, a housing having a patient input opening for establishing an air flow path of a patient being treated, said housing having an inlet opening including a one-way valve through which the patient draws inspiratory air substantially resistance free, said housing having a discharge outlet including a one-way valve through which the patient must pass expiratory air, an air flow controller carried by said housing and positioned in the air flow path to control the flow of expiratory air from the patient, said air flow controller including a first plate interposed in the path of expiratory air flow and having an orifice formed therein through which the expiratory air must pass and a second plate having at least two openings of different sizes formed therein which are mutually exclusively positionable in alignment with the orifice formed in said first plate for changing the size of the opening through which the expiratory air must pass to thereby induce an expiratory pressure in the patient's lungs, a pressure monitor actuable in response to expiratory air pressure applied thereto, said pressure monitor including a pressure chamber having a movable seal displaceable in response to expiratory air pressure applied to said pressure chamber, an expiratory air pressure transmitting conduit coupled between said housing and said air pressure monitor to transmit expiratory air pressure from said housing to said pressure chamber, an indicia display indicator operatively connected to said movable seal for movement in response thereto providing indicia for a patient to monitor expiratory air pressure, and a compression spring coaxially positioned about said indicator to apply a biasing force thereto against the movement of said movable seal.

10. The respiratory therapy device defined by claim 9 wherein said compression spring provides substantially linear movement of said indicator in response to expiratory pressure applied to said pressure chamber.

* * * * *